US010264190B2

United States Patent
Rastegar et al.

(10) Patent No.: US 10,264,190 B2
(45) Date of Patent: Apr. 16, 2019

(54) ADAPTIVE OPTICAL METHODS AND DEVICES FOR ENHANCING IMAGE CONTRAST IN THE PRESENCE OF BRIGHT BACKGROUND

(71) Applicant: Omnitek Partners LLC, Ronkonkoma, NY (US)

(72) Inventors: Jahangir S Rastegar, Stony Brook, NY (US); Harbans Dhadwal, Setauket, NY (US); Dake Feng, Kings Park, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 0 days.

(21) Appl. No.: 15/130,945

(22) Filed: Apr. 16, 2016

(65) Prior Publication Data

US 2016/0316127 A1 Oct. 27, 2016

Related U.S. Application Data

(60) Provisional application No. 62/152,596, filed on Apr. 24, 2015.

(51) Int. Cl.
| | |
|---|---|
| *H04N 5/235* | (2006.01) |
| *H04N 5/225* | (2006.01) |
| *G02B 26/08* | (2006.01) |
| *G02B 23/24* | (2006.01) |
| *H04N 5/238* | (2006.01) |
| *H04N 5/232* | (2006.01) |

(52) U.S. Cl.
CPC ......... *H04N 5/2355* (2013.01); *G02B 23/243* (2013.01); *G02B 23/2484* (2013.01); *G02B 26/0816* (2013.01); *H04N 5/2256* (2013.01); *H04N 5/2258* (2013.01); *H04N 5/238* (2013.01); *H04N 5/23293* (2013.01); *H04N 2005/2255* (2013.01)

(58) Field of Classification Search
CPC ............. G02B 23/243; G03H 2222/53; G03H 2240/61; G03H 2225/12; G03H 2210/22; G03H 2001/0224; G01N 2201/0675; H04N 5/2258
See application file for complete search history.

(56) References Cited

U.S. PATENT DOCUMENTS

| | | | |
|---|---|---|---|
| 6,438,396 B1 * | 8/2002 | Cook | A61B 5/0059 600/310 |
| 6,545,758 B1 * | 4/2003 | Sandstrom | B82Y 30/00 250/458.1 |

* cited by examiner

*Primary Examiner* — Nelson D. Hernández Hernández

(57) ABSTRACT

A device including: an image sensor for imaging an object field reflected from an object to be imaged; a first objective lens for focusing a background field from the object into a concentrated energy field on a spatial frequency plane of the first objective lens; and a programmable spatial light modulator positioned in an optical path at the spatial frequency plane, the programmable spatial light modulator being programmed to display an opaque region and a substantially transparent region outside of the opaque region, the opaque region corresponding to a position of the concentrated energy field.

12 Claims, 6 Drawing Sheets

ADAPTIVE OPTICAL METHODS AND DEVICES FOR ENHANCING IMAGE CONTRAST IN THE PRESENCE OF BRIGHT BACKGROUND

CROSS REFERENCE TO RELATED APPLICATION

This application claims benefit of U.S. Provisional Application No. 62/152,596 filed on Apr. 24, 2016, the entire contents of which is incorporated herein by reference.

BACKGROUND

1. Field

The present invention relates generally to adaptive methods and devices for enhancing image contrast in the presence of bright background, and more particularly to image contrast enhancing methods and devices for the entire range of endoscopy, and other similar devices used for imaging bright field objects, such as, human tissue, highly reflective semiconductor elements on wafers or MEM structures or the like.

2. Prior Art

The extraction of high contrast images of objects buried in a bright field background, such as those encountered in endoscopy and other similar medical devices and in devices used for imaging micro- or nano-scale objects such as MEMS devices continues to challenge the entire optical imaging industry.

All existing solutions to date are mostly based on processing the digital images that are obtained after optical detection. However, this is a losing battle as the object information, which may have a total energy content of less than 1%, has been lost during optical detection and quantization. Additionally, the other 99% of the energy from the background adds significant shot noise during the optical detection process, further reducing the signal to noise ratio and image contrast.

SUMMARY

A need therefore exists for methods and devices for significantly enhancing image contrast in the presence of bright background in devices such as various endoscopy and other similar medical devices and for imaging bright field objects, such as, human tissue, devices on highly reflective semiconductor wafers or MEM structures or the like.

A need also exists for methods and devices for significantly enhancing image contrast when the light source in the said devices is a single wavelength coherent light source. Such devices are widely used in medical and other industrial and commercial applications in which the captured imaging do not have to be in color to serve their intended purposes.

A need also exists for adaptive methods and devices for significantly enhancing image contrast when the light source in the said devices is a single wavelength coherent light source and the surface of the object may be viewed as a collection of "relatively discrete" "effective reflective surfaces" which reflect the incoming coherent light in the same direction. Such objects are widely encountered in the medical field as different tissues when using endoscopy for diagnosis purposes or during laparoscopic surgery.

A need also exists for methods and devices for significantly enhancing image contrast when the captured images have to be in color to serve their intended user purposes, such as during laparoscopic surgery.

A need also exists for methods and devices for significantly enhancing image contrast in various devices such as endoscopy and other similar medical devices and for imaging bright field objects, such as, human tissue, devices on highly reflective semiconductor wafers or MEM structures or the like using white light illumination sources.

A need also exists for devices for enhancing imaging contrast that can be readily attached to existing endoscopy and other similar aforementioned devices without requiring any change or modification to be made to such devices. As such, any user should be able to incorporate the present devices into their endoscopy and other similar devices with minimal effort.

A need also exists for devices for enhancing imaging contrast that can be used for visual inspection of nano- and micro-devices and other structures on silicon wafers and other micro- and nano-structures and devices that are machined or etched or deposited or the like on other types of material substrates and the like that share the same problems of imaging microscopic features on highly reflective surfaces.

The present methods and devices for enhancing images can be used to enhance imaging contrast in many devices, including medical devices such as medical endoscopy devices. Hereinafter, the methods and devices will be described mostly as applied to medical endoscopy systems without intending to limit the described methods and devices to such endoscopy systems.

Accordingly, novel methods and novel classes of optical imaging devices that would enhance image contrast in the presence of a bright field by orders of magnitude are provided. The disclosed method and devices can be used in devices with single wavelength coherent light sources. The disclosed novel methods and devices provide innovative optical solution to significantly enhance imaging contrast under coherent (single wavelength illumination) as well as under incoherent illumination (multi-wavelength illumination or white light), through rejection of the background optical energy.

Also provided is methods and devices that can be used in endoscopy and other aforementioned similar devices to provide high contrast full color images.

The user base for the present novel adaptive methods and devices for image contrast enhancement is very broad and may be separated into two basic categories: in vivo cellular imaging and visual inspection of nano- and micro-structures and the like. The provision of images with orders of magnitude better contrast in the former category will have a profound effect on the quality of services provided to patients in need of medical procedures using endoscopy and confocal endomicroscopy for the early discovery of disease, and in vivo optical biopsy and minimally invasive surgery. Some of these procedures are gastrointestinal tract infections, Barrett's Esophagus, celiac diseases, inflammatory bowel disease, colorectal cancer, gastric cancer, urinary tract, cervical intraepithelial neoplasia, ovarian cancer, head and neck and lung. The surgeons performing the above procedures are generally dissatisfied with the image contrast of existing devices and are demanding high contrast images, in particular, for improving the contrast of images during laparoscopic surgery. Enhanced image contrast is a sought out metric for users of biomedical imaging systems. An increase of up to two orders of magnitude in imaging contrast which is achievable using the disclosed novel methods and devices will have direct consequence on the productivity of surgeons and should significantly reduce the chances of damage to peripheral tissue and nerves. Using such contrast enhanced imaging systems, the medical professionals will be able to identify disease earlier, reduce the number of repeat procedures and improve surgical margin detection.

In one embodiment of the present invention, an adaptive method is disclosed for enhancing the contrast of the image by using a second camera to capture the image of the frequency plane. This information is used to program a spatial light modulator prior to capturing the contrast enhanced image.

In another embodiment of the present invention, a method is provided for capturing the image of the frequency plane without the use of a second camera.

BRIEF DESCRIPTION OF THE DRAWINGS

These and other features, aspects, and advantages of the apparatus of the present invention will become better understood with regard to the following description, appended claims, and accompanying drawings where:

DETAILED DESCRIPTION

Figure 1:
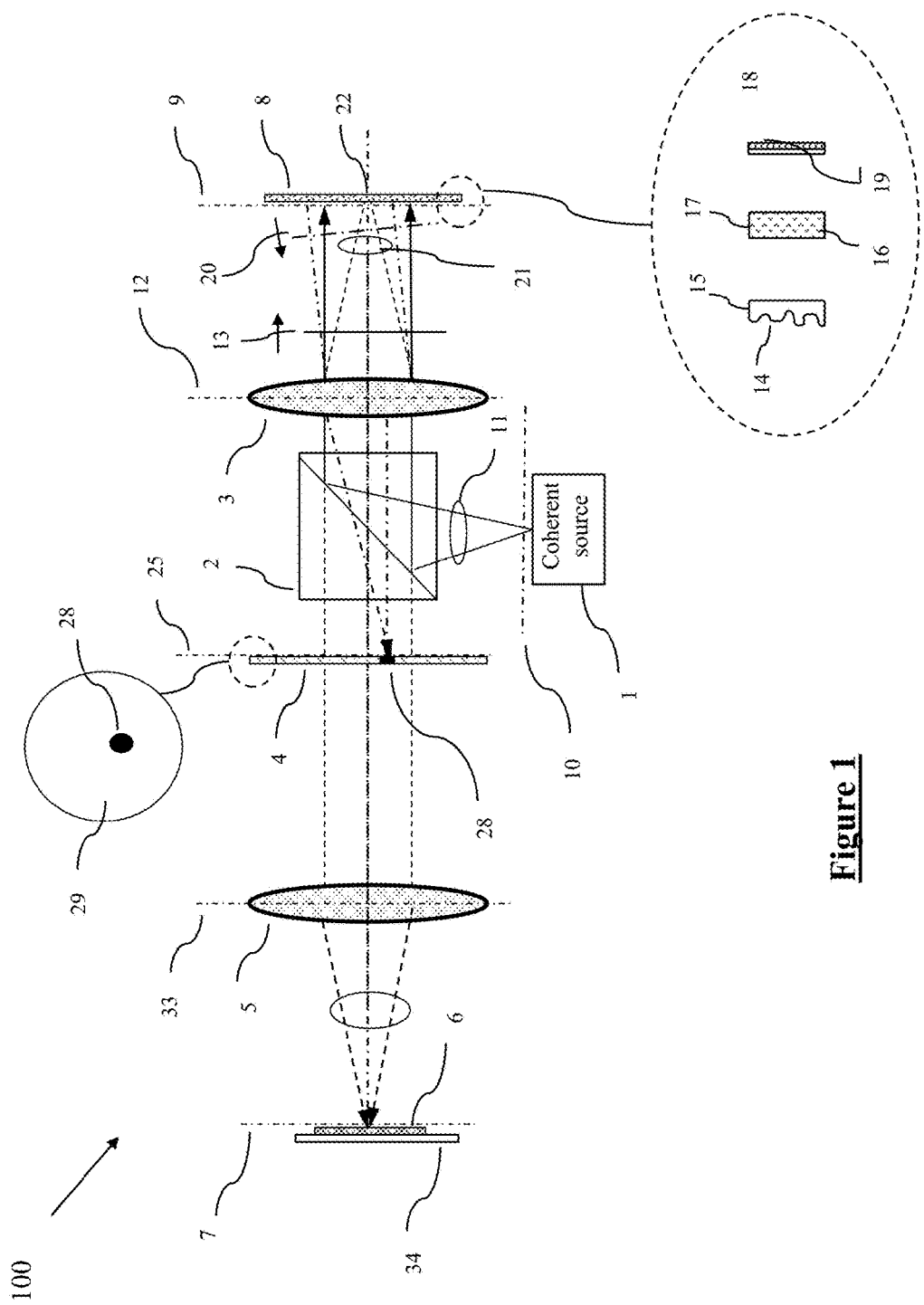
FIG. 1 illustrates a schematic of a coherent image contrast enhancer.

The embodiments and the method of developing them may be divided into the following two classes. The primary objective of these two classes of optical imaging methods and devices is to significantly enhance image contrast in general, and in the presence of bright illumination field, mostly by up to two orders of magnitude or even better. This is a conservative estimate, based on a background to object power level of a 100. Typically, the enhancement factor is going to be larger for stronger background signals. The upper limit is determined by the extinction efficiency of the opaque block placed in the frequency plane.

The first novel class of optical imaging methods and devices belong to those for use in systems that utilize a single wavelength coherent light source for object illuminations. Hereinafter, the optical imaging devices belonging to this class are referred to as "Coherent Image Contrast Enhancers" (CICE). This class of optical imaging devices would also significantly enhance imaging contrast when the object is subjected to white light illumination.

The second novel class of optical imaging methods and devices belong to those that use multi-wavelength coherent light sources for object illumination for the purpose of providing high contrast imaging in a certain range or even in full color. Hereinafter, the optical imaging devices belonging to this class are referred to as "Color-Coherent Image Contrast Enhancers" (CCICE), which can be designed and fabricated as an attachment, which would easily mate to the proximal end of conventional endoscopes and microscopes and the like replacing either the eyepiece or the imaging lens depending on the endoscope design, without requiring any modification to the devices. The CCICE devices would enable full color in vivo imaging of bright field objects, such as, human tissue, highly reflective semiconductor wafers or MEM structures or the like. This class of optical imaging devices would also significantly enhance imaging contrast when the object is subjected to white light illumination.

In relation to endoscopy and the like devices used in the medical field and the aforementioned industrial areas, the industry is moving toward modular laparoscopic instruments, with the introduction of tools such as improved imaging systems, 3D laparoscopic instruments, multiple robotic devices and other new instruments are over the horizon. The novel methods and devices presented herein would provide a significant improvement in the full range of endoscopic devices by an order of magnitude improvement in their imaging contrast. As an example, the rapidly increasing field of minimally invasive surgery would greatly benefit from such imaging contrast enhancement that can be achieved during laparoscopic surgery is live feed of in vivo optical images. Similarly and as an example, in industries designing and fabricating nano- and micro-scale devices, the provision of the means to significantly enhance imaging contrast in inspection, quality control, fabrication and assembly equipment would significantly increase production efficiency and quality as well as cost.

The novel methods and device embodiments presented herein recognize that the object function has a broad higher spatial frequency spectrum in comparison with the narrow spectrum of a bright background illumination. Consequently, the bright background illumination appears as a point in the spatial frequency plane, whereas the object energy distributes over the entire frequency plane. The location of the focused spot, in the frequency plane, is a function of the illumination. Thus, an opaque (or graded transmission or reflecting) disk, positioned at the optimal location in the spatial frequency plane should block transmission of the bright field to the image plane. In the different embodiments presented herein, the imaging system separates the object function from the bright field, thereby allowing for full use of the dynamic range of the detector and quantizer and making it possible to achieve high contrast imaging. It will be appreciated by those skilled in the art that almost all currently available image enhancing software algorithms may still be utilized for processing the captured image data.

Hereinafter, the different embodiments for each one of the aforementioned two classes of optical imaging methods and devices are described in detail.

The first embodiment 100 (disclosed in provisional patent application No. 62/028,779 and incorporated herein by reference) of the aforementioned first class of optical imaging methods and devices of the present invention is described with reference to the illustrations of FIGS. 1 and 2. The optical imaging device of FIG. 1 is shown to comprise of a single wavelength coherent source 1, preferably a laser diode, a beam splitter 2, an objective lens 3, a spatial light filter 4 and an imaging lens 5. The optical imaging device 100 provides a means for forming a high contrast image 6, located in the front focal plane 7 of the imaging lens 5, of the object 8 located in the front focal plane 9 of the objective lens 3. The coherent source 1, located in the back focal plane 10 of the objective lens 3 produces a diverging wave field 11, whose direction changes by means of a beam splitter 2. The objective lens 3, located in the plane 12 produces a collimated wavefield 13, which illuminates the object 8, located in the front focal plane 9 of the objective lens 3. As can be seen in the close-up view of FIG. 1, here either the amplitude features 14 etched on a highly reflective surface 15, or cellular structures 16 within a tissue sample 17, or fluorescent molecules 18 attached to a glass surface 19, or the like is considered to define object features.

Figure 2:
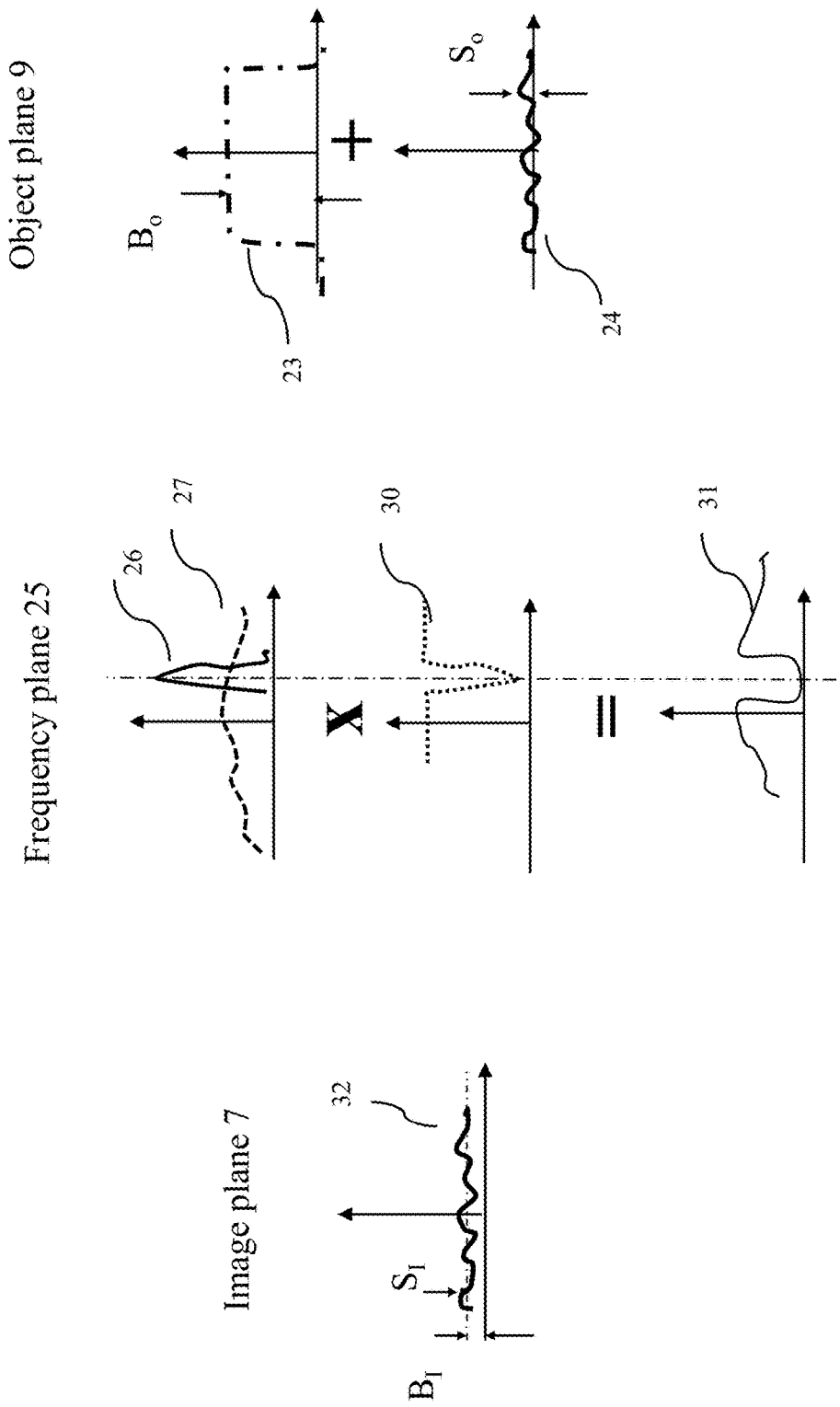
FIG. 2 illustrates typical intensity profiles at the "object plane", "frequency plane" and "image plane" of the optical imaging embodiment of FIG. 1.

Referring to FIGS. 1 and 2, typically, two wavefields emanate from the object 8 in response to the collimated illumination 13: a background optical wavefield 20, which is essentially a plane wave, possibly not parallel to the optical axis, and a diverging wave field 21 from any spatial feature 22 of the object 8. Typically, the wavefield, in a coherent system, is characterized by a complex amplitude, expressed in a plane transverse to the direction of propagation. The intensity 23, which is proportional to the square of the complex amplitude, of the background wavefield 20 is much stronger than the intensity 24 of the object features. When this type of object or the like is captured using a two-dimensional photo-detector of a conventional imaging system, the image contrast is proportional $S_O/B_O$ much smaller than unity.

The complex amplitude in the back focal plane 25, referred to as the spatial frequency plane, of the objective lens 3, preferably a converging lens, is proportional to the Fourier transform of the complex amplitude in the front focal plane 9. The complex amplitude in the spatial frequency plane 25 is a superposition of the Fourier transforms of the object 24 and background 23 complex amplitudes in the object plane 9 (FIG. 2). The uniform bright object background transforms into a narrow distribution 26 in the spatial frequency plane 25 (FIG. 2), while the object wavefield 24 transforms to a wider distribution 27 in frequency plane 25 (FIG. 2). A spatial filter 4, FIG. 1, with an opaque region 28 and a transparent region 29, placed at the location spatial frequency plane 25 (see the close-up view in FIG. 1), with transmittance 30 (FIG. 2) selectively removes the low frequency components of the composite complex amplitude in the spatial frequency plane. The complex amplitude 31 (FIG. 2), immediately behind the spatial frequency filter 4, corresponds to the frequency components representing the object features 14 or 16 or 18 or the like (see the close up view in FIG. 1). The complex amplitude 32 (FIG. 2) in the front focal plane 7 of the imaging lens 5 located at plane 33 is a high contrast image of the object 24. A photo-detector 34 can then record the resulting high contrast image, that is, $S_I$ is larger than the background BI.

Figure 3:
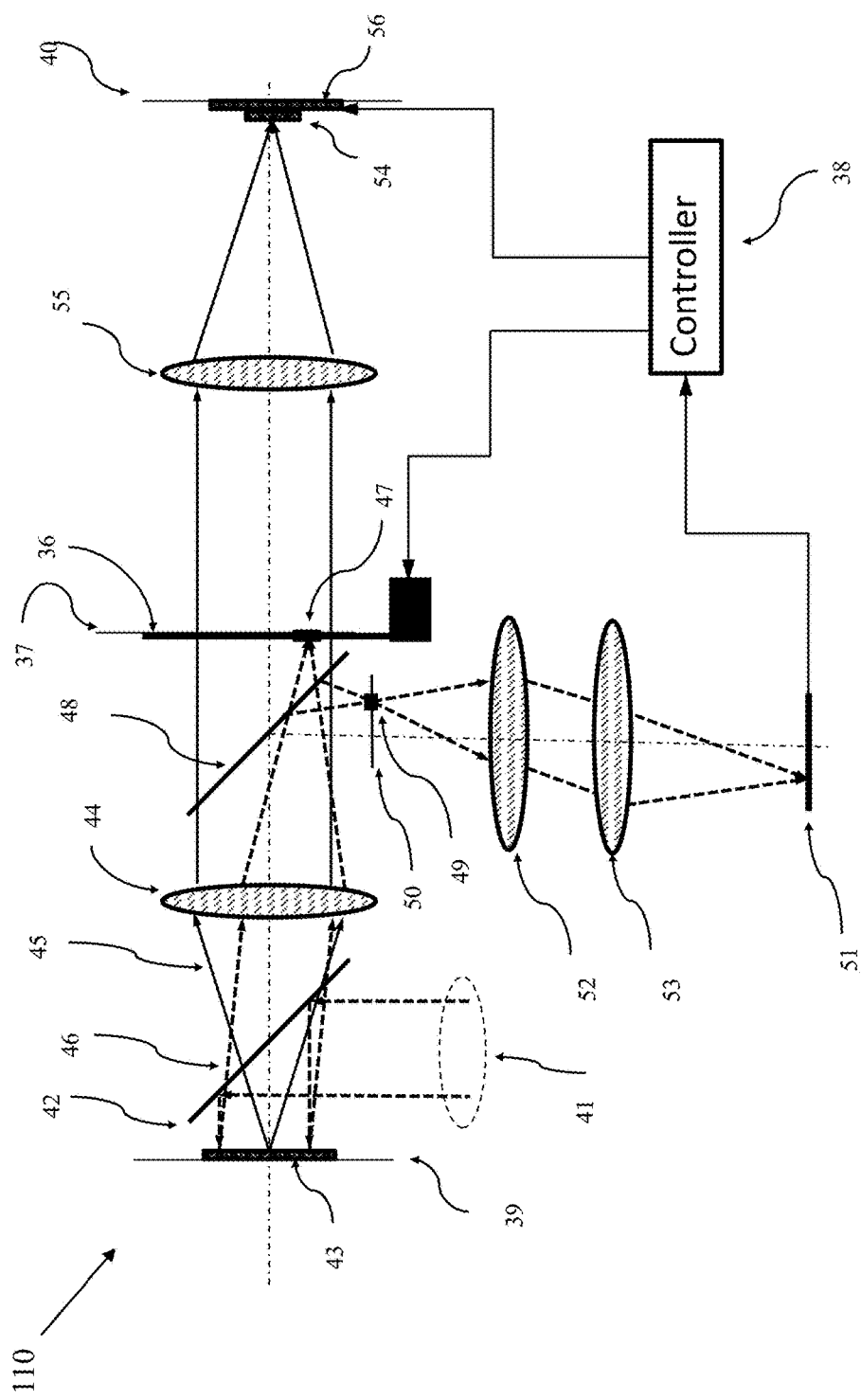
FIG. 3 illustrates the schematic of the first embodiment of the optical imaging methods and devices of the present invention.

FIG. 3 illustrates the functional block diagram of the first embodiment 110 of the coherent image contrast enhancer device, in which the spatial filter 4 located in the spatial frequency plane 25 of FIG. 1 is replaced by a programmable spatial light modulator (SLM) 36 located in the frequency plane 37. The SLM 36 can be programmed through a controller 38 to adaptively modify the amplitude of the wavefield as it passes from the object plane 39 to the image plane 40. The design and operation of the coherent image contrast enhancer device described here, includes a coherent collimated source 41, which reflects from a beam splitter 42 to uniformly illuminate the object 43 located in the front focal plane 39 of the objective lens 44. The optical field emanating from the object plane is composed of the object field 45 and a bright background field 46. The background field 46 produces a concentrated energy field 47 in the spatial frequency plane 37 located in the back focal pane of the objective lens 44. A partially reflecting beam splitter 48 forms a real image 49 of the concentrated energy spot 47 on a screen 50. This intermediate image 50 is projected on to the surface of a digital camera 51 (first image sensor, such as a CMOS or CCD) using a pair of converging lenses 52 and 53. The captured image is a replica of the frequency plane distribution 47 of the bright field background 46. The captured image 51 is used to program the SLM 36 for blocking the transmission of one or more concentrated energy spots 47. A controller system 38 provides the digital interface to actively program the SLM 36, whose transmittance characteristics, both amplitude and phase, can be changed at will. Subsequently, the high contrast image 54 of the object 43 is captured by an imaging lens 55 and a second digital camera 56 (second image sensor, such as a CMOS or CCD).

Figure 4:
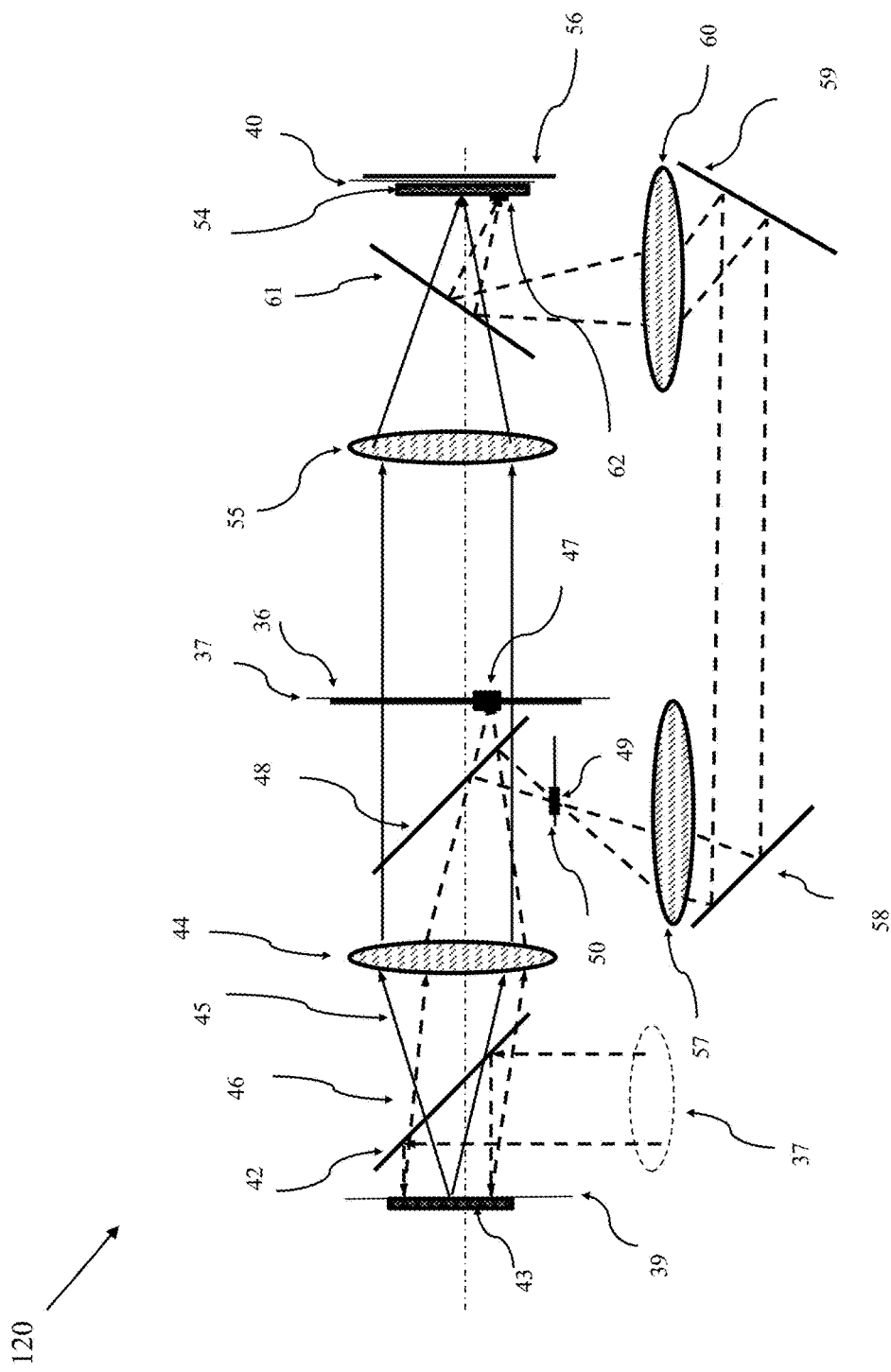
FIG. 4 illustrates the schematic of the second embodiment of the optical imaging methods and devices of the present invention.

FIG. 4 illustrates the functional block diagram of a second embodiment 120 of the coherent image contrast enhancer device, which uses a single digital camera 56 (image sensor, such as a CMOS or CCD) for sequentially recording the image of the frequency plane distribution 47 and the contrast enhanced image 54 of the object 43. Functionally, this third embodiment is the same as the second embodiment (FIG. 3) described above. However, by folding the spatial frequency plane imaging optics as described below, the third embodiment requires only one digital camera. The intermediate real image 49 of the frequency plane distribution 47 corresponding to the bright background 46 is projected on screen 50 and is collimated by lens 57, folded by mirrors 58 and 59, imaged by lens 60 and reflected by beam splitter 61 on to the surface of the digital camera 56 to the spatial location 62. In this embodiment, the high contrast image requires a two-step procedure: step 1 captures the spatial frequency image 47 of the bright background 46 with the transmittance of the SLM set to unity for the entire spatial frequency plane. Subsequently, the location of all the concentrated light spots in the spatial frequency plane are extracted from the recorded image 54 and subsequently, the transmittance of the SLM 36 is adaptively updated. With these optimal settings of the SLM, step 2 captures the high contrast image 54 of the object 43.

Figure 5A:
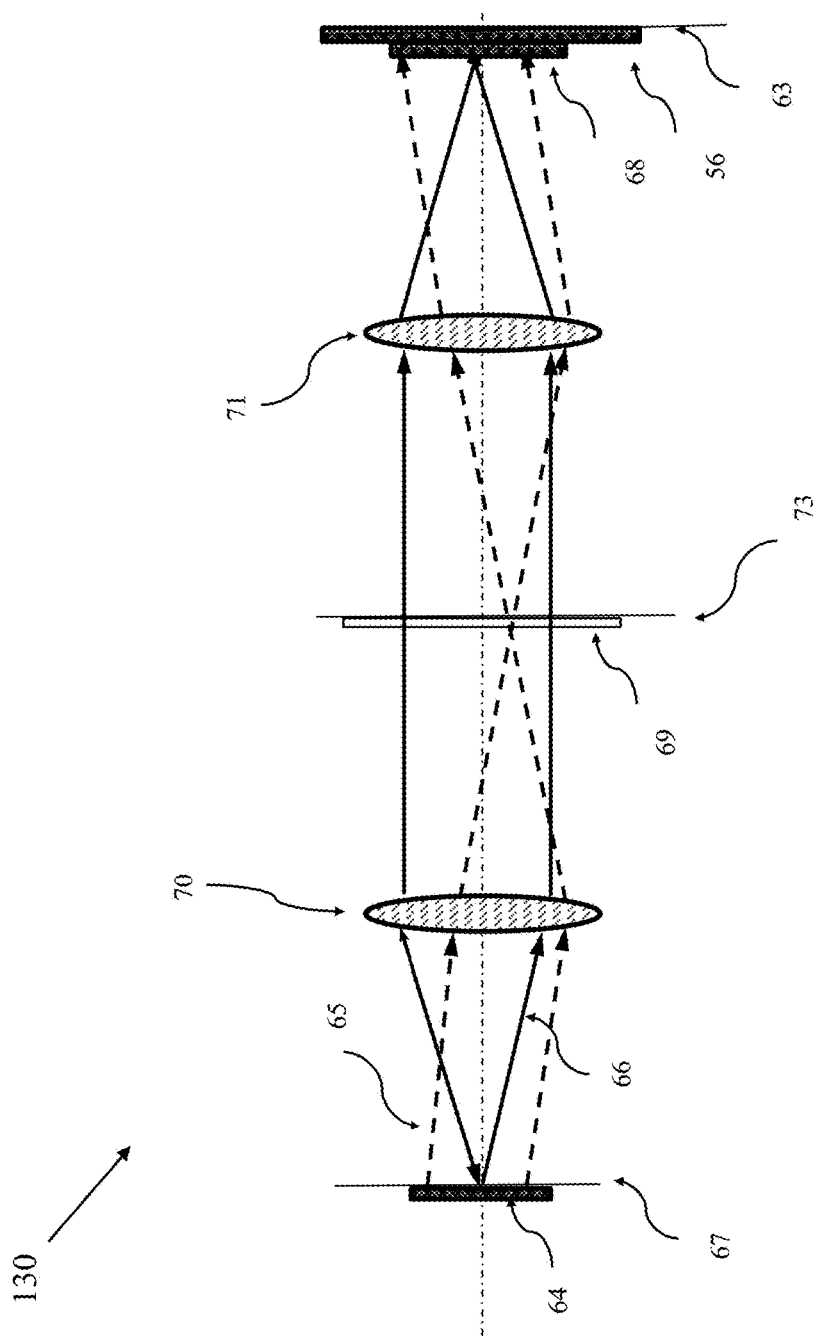
FIGS. 5a and 5b illustrates the schematic of the third embodiment of the optical imaging methods and devices of the present invention as applied to an endoscope with a camera end.

FIG. 5a illustrates the functional block diagram of the third embodiment 130 of the coherent image contrast enhancer device, which uses one digital camera 56 (image sensor), located in the image plane 63. Functionally, while this fourth embodiment is the same as third embodiment 120 (FIG. 4), it differs in two distinct ways: 1) the folding optics for capturing the real spatial frequency plane image are omitted and 2) the single wavelength illumination source has been separated from the imaging optics. The separation of the illuminating source and the imaging optics is quite common, for example, in laparoscopic surgery. Typically, the light sources and imaging optics are introduced into body cavities through separate ports or separate lumens/channels of the same instrument.

For such situations, the combined optical field emitted from the illuminated object 64, for example human tissue, comprises of a bright background 65 and the object field 66, located at the object plane 67. Embodiment four represents a substantial reduction in the complexity of the optical system and makes it attractive for use as a retro-fit attachment to existing imaging systems, such as those that are endoscope based.

Figure 5B:
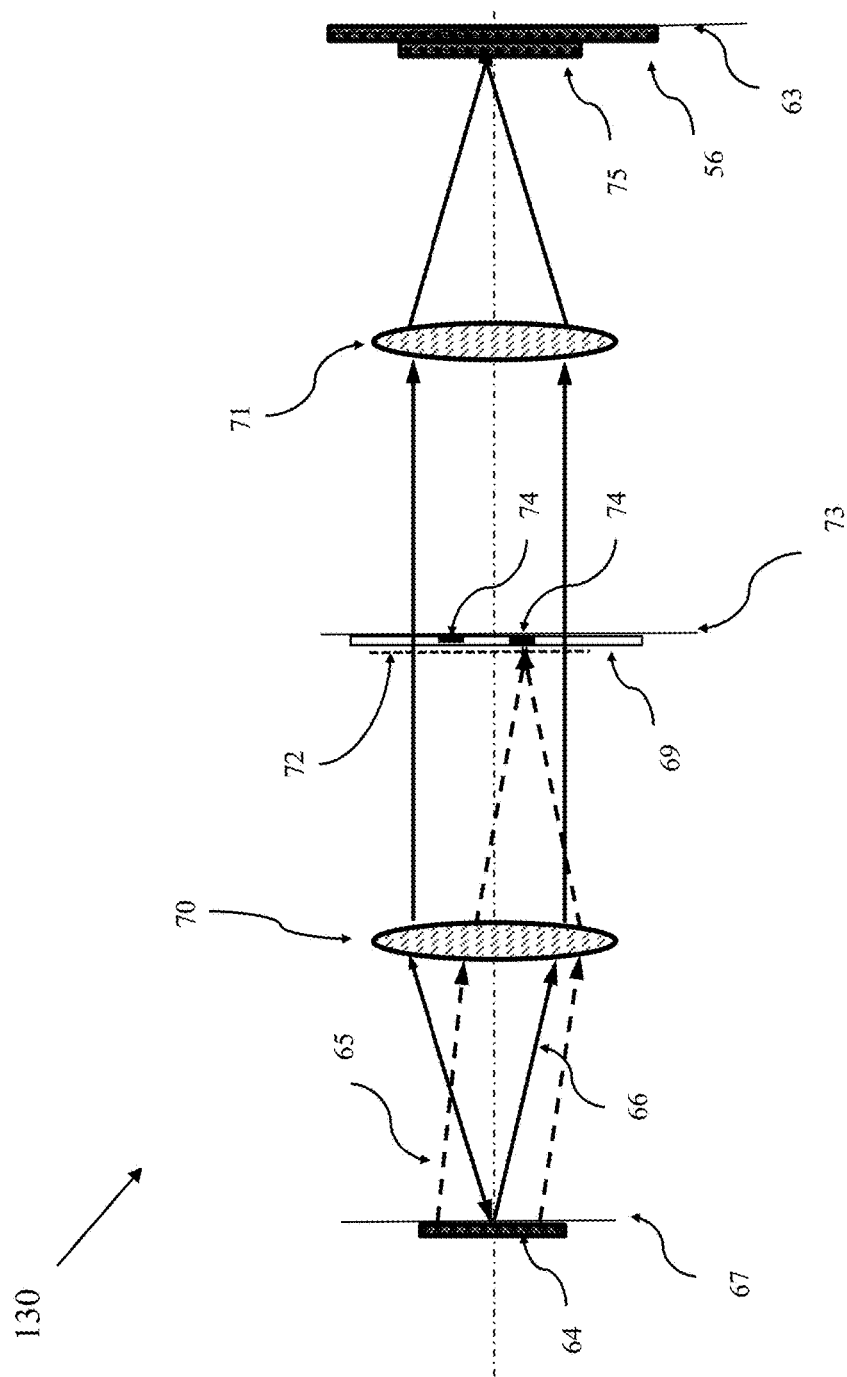

Capturing high contrast images in the presence of a bright field is a three-step process. Step 1 captures the expected low contrast image 68 of the object 64, with the SLM 69 programmed with a unity transmittance function, using the 4-f system formed by the objective lens 70 and image lens 71. Referring to FIGS. 5a and 5b, Step 2 extracts the spatial Fourier transform of the low contrast image 68, which corresponds to the spatial distribution 72 in the frequency plane 73, giving the location of all the concentrated light spots 74 in the spatial frequency plane. The Fourier transform of image 68 can be implemented using either dedicated hardware or software. Step 3 programs the SLM 69 to block the transmission of the bright background signals at the preferred locations 74 determined in step 2. The captured image 75 is subsequently a high contrast image of the object field 66 only.

In the above embodiments of the present invention, the imaging systems use a single wavelength source for obtaining a high contrast image of an object with a bright background. In some applications, however, it may be desirable to have multiple single wavelength sources to achieve improvement on the imaging contrast by, for example, introducing excitation of various contrasting agents or by introducing certain range of colors or achieve a high contrast white light image as disclosed in provisional patent application provisional patent application No. 62/028,779.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A device comprising:
   an image sensor for imaging an object field reflected from an object to be imaged;
   a first objective lens for focusing a background field from the object into a concentrated light spot on a spatial frequency plane of the first objective lens;
   a programmable spatial light modulator positioned in an optical path at the spatial frequency plane, the programmable spatial light modulator being programmed to display an opaque region and a substantially transparent region outside of the opaque region, the opaque region corresponding to a position of the concentrated light spot; and
   a controller operatively connected to the programmable spatial light modulator, the controller:
      determining the position on the programmable spatial light modulator to display the opaque region such that the concentrated light spot is at least partially blocked from being incident on the image sensor; and
      controlling the programmable spatial light modulator to display the opaque region at the position.

2. The device of claim 1, further comprising a light source for outputting illumination light to the object to be imaged, the object reflecting both the object field and the background field.

3. The device of claim 1, further comprising a second objective lens for focusing the object field on a surface of the image sensor.

4. The device of claim 1, further comprising:
   a display screen;
   first and second objective lens;
   first and second mirrors;
   a first beam splitter positioned between the first objective lens and the programmable spatial light modulator to project the concentrated light spot onto the display screen;
   the first objective lens projecting the concentrated light spot on the display screen onto the first mirror;
   the second mirror reflecting the concentrated light spot from the first mirror towards the second objective lens;
   the second objective lens projecting the concentrated light spot towards a second beam splitter;
   the second beam splitter positioned to project the concentrated light spot on the image sensor when the programmable spatial light modulator is not displaying the opaque region;
   wherein the controller determines the location of the concentrated light spot on the image sensor; and
   the controller determines the position on the programmable spatial light modulator to display the opaque region based on the location of the concentrated light spot on the image sensor.

5. The device of claim 1, wherein:
   the image sensor captures a low contrast image of the object when the programmable spatial light modulator is not displaying the opaque region; and
   the controller extracts a spatial Fourier transform of the low contrast image corresponding to a spatial distribution in the spatial frequency plane and controls the programmable spatial light modulator to display the opaque region based on the spatial Fourier transform.

6. A device of claim 4, further comprising:
   an image sensor for imaging an object field reflected from an object to be imaged;
   a first objective lens for focusing a background field from the object into a concentrated energy field on a spatial frequency plane of the first objective lens; and
   a programmable spatial light modulator positioned in an optical path at the spatial frequency plane, the programmable spatial light modulator being programmed to display an opaque region and a substantially transparent region outside of the opaque region, the opaque region corresponding to a position of the concentrated energy field;
   a controller operatively connected to the programmable spatial light modulator, the controller:
      determining the position on the programmable spatial light modulator to display the opaque region such that the concentrated energy field is at least partially blocked from being incident on the image sensor; and
      controlling the programmable spatial light modulator to display the opaque region at the position;
   a display screen;
   an other image sensor;
   a beam splitter positioned between the first objective lens and the programmable spatial light modulator to project the concentrated energy field on the display screen; and
   one or more additional objective lens for projecting the concentrated energy field on the screen onto the other image sensor;
   wherein the other image sensor is operatively connected to the controller for inputting the location of the concentrated energy field on the other image sensor; and
   the controller determines the position on the programmable spatial light modulator to display the opaque region based on the location of the concentrated energy field on the other image sensor.

7. A method comprising:
   imaging an object field reflected from an object to be imaged;
   focusing a background field from the object into a concentrated light spot on a spatial frequency plane;

displaying an opaque region at the spatial frequency plane on a programmable spatial light modulator, the opaque region corresponding to a position of the concentrated light spot;

determining the position on the programmable spatial light modulator to display the opaque region such that the concentrated light spot is blocked from being incident on the image sensor; and controlling the programmable spatial light modulator to display the opaque region at the position.

8. The method of claim 7, further comprising outputting illumination light to the object to be imaged, the object reflecting both the object field and the background field.

9. The method of claim 7, further comprising focusing the object field on a surface of an image sensor.

10. The method of claim 7, further comprising:

projecting the concentrated light spot on the image sensor when the programmable spatial light modulator is not displaying the opaque region;

determining a location of the concentrated light spot on the image sensor; and determining the position on the programmable spatial light modulator to display the opaque region based on the location of the concentrated light spot on the image sensor.

11. The method of claim 7, further comprising:

capturing a low contrast image of the object on the image sensor when the programmable spatial light modulator is not displaying the opaque region;

extracting a spatial Fourier transform of the low contrast image corresponding to a spatial distribution in the spatial frequency plane; and controlling the programmable spatial light modulator to display the opaque region based on the spatial Fourier transform.

12. A method comprising:

imaging an object field reflected from an object to be imaged;

focusing a background field from the object into a concentrated energy field on a spatial frequency plane; and displaying an opaque region at the spatial frequency plane on a programmable spatial light modulator, the opaque region corresponding to a position of the concentrated energy field;

determining the position on the programmable spatial light modulator to display the opaque region such that the concentrated energy field is blocked from being incident on the image sensor;

controlling the programmable spatial light modulator to display the opaque region at the position;

projecting the concentrated energy field onto an other image sensor; and determining the position on the programmable spatial light modulator to display the opaque region based on the location of the concentrated energy field on the other image sensor.

* * * * *